United States Patent [19]
Davis

[11] Patent Number: 6,045,531
[45] Date of Patent: Apr. 4, 2000

[54] CATHETER HAVING A LUMEN OCCLUDING BALLOON AND METHOD OF USE THEREOF

[75] Inventor: Albert Davis, Richardson, Tex.

[73] Assignee: Chase Medical Inc., Richardson, Tex.

[21] Appl. No.: 09/121,617

[22] Filed: Jul. 22, 1998

Related U.S. Application Data

[60] Provisional application No. 60/053,416, Jul. 22, 1997.

[51] Int. Cl.⁷ .................................................. A61M 29/00
[52] U.S. Cl. ............................................. 604/101; 604/96
[58] Field of Search .............................. 604/96–101, 264, 604/280; 606/191–2, 194

[56] References Cited

U.S. PATENT DOCUMENTS

| | | |
|---|---|---|
| Re. 35,352 | 10/1996 | Peters . |
| Re. 35,459 | 2/1997 | Jonkman . |
| 2,701,559 | 2/1955 | Cooper . |
| 3,640,282 | 2/1972 | Kamen et al. . |
| 4,129,129 | 12/1978 | Amrine . |
| 4,328,056 | 5/1982 | Snooks . |
| 4,413,989 | 11/1983 | Schjeldahl et al. . |
| 4,417,576 | 11/1983 | Baran . |
| 4,531,936 | 7/1985 | Gordon . |
| 4,592,340 | 6/1986 | Boyles . |
| 4,596,552 | 6/1986 | DeVries . |
| 4,601,706 | 7/1986 | Aillon . |
| 4,610,662 | 9/1986 | Weikl et al. . |
| 4,648,384 | 3/1987 | Schmukler . |
| 4,676,778 | 6/1987 | Nelson, Jr. . |
| 4,689,041 | 8/1987 | Corday et al. . |
| 4,741,328 | 5/1988 | Gabbay . |
| 4,781,682 | 11/1988 | Patel . |
| 4,927,412 | 5/1990 | Menasche . |
| 4,943,277 | 7/1990 | Bolling . |
| 4,988,515 | 1/1991 | Buckberg . |
| 5,011,469 | 4/1991 | Buckberg et al. . |
| 5,013,296 | 5/1991 | Buckberg et al. . |
| 5,021,045 | 6/1991 | Buckberg et al. . |
| 5,024,668 | 6/1991 | Peters et al. . |
| 5,033,998 | 7/1991 | Corday et al. . |
| 5,090,960 | 2/1992 | Don Michael . |
| 5,135,474 | 8/1992 | Swan et al. . |
| 5,135,484 | 8/1992 | Wright . |
| 5,149,330 | 9/1992 | Brightbill . |
| 5,151,087 | 9/1992 | Jonkman . |

(List continued on next page.)

FOREIGN PATENT DOCUMENTS

| | | |
|---|---|---|
| 0 218 275 | 8/1986 | European Pat. Off. . |
| 0 280 25 | 2/1988 | European Pat. Off. . |
| 0 415 332 A1 | 8/1990 | European Pat. Off. . |
| 0 704 226 A1 | 4/1996 | European Pat. Off. . |
| 0 769 307 A2 | 4/1997 | European Pat. Off. . |
| WO 92/20398 | 11/1992 | WIPO . |
| WO 95/11719 | 10/1994 | WIPO . |
| WO 95/28983 | 11/1995 | WIPO . |
| WO 9717099 | 10/1996 | WIPO . |

*Primary Examiner*—Wynn Wood Coggins
*Assistant Examiner*—Jennifer R. Sadula
*Attorney, Agent, or Firm*—Robert C. Klinger

[57] ABSTRACT

A catheter and method of use adapted to intermittently deliver fluids to and drain fluids from a body vessel having an interior lumen occluding balloon. The selective inflation and deflation of the inner balloon controls the occlusion or communication of an inner lumen. The inner occluding balloon is defined between the distal end of the catheter and a proximal lumen opening allowing for the selective isolation of the proximal openings from the catheter distal end. The catheter of the present invention and several methods of use thereof are ideally suited for aortic perfusion and providing myocardial infusion in antegrade fashion using a single lumen. The catheter is further provided with a double lobed outer balloon for selectively occluding the body vessel, such as the aorta, and to provide a bloodless region to complete the proximal end of an anastomosis while perfusing the myocardium to restart the heart.

7 Claims, 5 Drawing Sheets

U.S. PATENT DOCUMENTS

| | | |
|---|---|---|
| 5,167,628 | 12/1992 | Boyles . |
| 5,171,218 | 12/1992 | Fonger et al. . |
| 5,197,952 | 3/1993 | Marcadis et al. . |
| 5,213,576 | 5/1993 | Abiuso et al. . |
| 5,221,258 | 6/1993 | Shturman . |
| 5,290,231 | 3/1994 | Marcadis et al. . |
| 5,308,323 | 5/1994 | Sogawa et al. . |
| 5,312,344 | 5/1994 | Grinfeld et al. . |
| 5,324,260 | 6/1994 | O'Neill et al. . |
| 5,334,142 | 8/1994 | Paradis . |
| 5,338,298 | 8/1994 | McIntyre . |
| 5,360,403 | 11/1994 | Mische . |
| 5,378,230 | 1/1995 | Mahurkar . |
| 5,395,330 | 3/1995 | Marcadis et al. . |
| 5,395,331 | 3/1995 | O'Neill et al. . |
| 5,423,745 | 6/1995 | Todd et al. . |
| 5,433,700 | 7/1995 | Peters . |
| 5,437,637 | 8/1995 | Lieber et al. . |
| 5,443,446 | 8/1995 | Shturman . |
| 5,443,448 | 8/1995 | DeVries . |
| 5,451,207 | 9/1995 | Yock . |
| 5,452,733 | 9/1995 | Sterman et al. . |
| 5,458,574 | 10/1995 | Machold et al. . |
| 5,458,575 | 10/1995 | Wang . |
| 5,478,309 | 12/1995 | Sweezer et al. . |
| 5,487,730 | 1/1996 | Marcadis et al. . |
| 5,501,667 | 3/1996 | Verduin, Jr. . |
| 5,505,598 | 4/1996 | Booth et al. . |
| 5,533,957 | 7/1996 | Aldea . |
| 5,558,644 | 9/1996 | Boyd et al. . |
| 5,571,215 | 11/1996 | Sterman et al. . |
| 5,584,803 | 12/1996 | Stevens et al. . |
| 5,597,377 | 1/1997 | Aldea . |
| 5,609,571 | 3/1997 | Buckberg et al. . |
| 5,611,775 | 3/1997 | Machold et al. . |
| 5,620,418 | 4/1997 | O'Neill et al. . |
| 5,658,311 | 8/1997 | Baden . |
| 5,662,620 | 9/1997 | Lieber et al. . |

CATHETER HAVING A LUMEN OCCLUDING BALLOON AND METHOD OF USE THEREOF

CROSS REFERENCE TO RELATED APPLICATIONS

Cross reference is made to the following co-pending patent applications, each being assigned to the same assignee as the present invention and the teachings incorporated herein by reference:

| Ser. No. | TITLE | FILING DATE |
| --- | --- | --- |
| 08/846,654 | METHOD OF USING INTEGRAL AORTIC ARCH INFUSION CLAMP | May 1, 1997 |
| 09/070,696 | INTEGRAL AORTIC ARCH INFUSION CLAMP HAVING PRESSURE PORTS | April 30, 1998 |
| 09/121,151 | CATHETER SYSTEM AND METHOD FOR POSTERIOR EPICARDIAL REVASCULARIZATION AND INTRACARDIAC SURGERY ON A BEATING HEART | HEREWITH |

FIELD OF THE INVENTION

The present invention is generally related to delivery and drainage catheters suitable for use in medical applications, and more particularly to catheters having the ability to selectively deliver or drain fluids to/from a body vessel in intermittent fashion.

BACKGROUND OF THE INVENTION

The use of medical catheters to administer fluids to and draw fluids out of the body has been a standard practice in medical procedures for years. The various catheters can be used independently or in combination with other catheters to provide different functions, for instance, for venting body fluids from one portion of the body and delivering another fluid via another catheter to a separate part of the body.

Often, there is a need to selectively deliver fluids to a body vessel, or drain fluids from a body vessel, in intermittent fashion. While there are many catheters and techniques to deliver and drain fluids in intermittent fashion, prior art devices have various advantages and disadvantages depending on the intended use of the catheter and the various features of the particular catheter.

There is a desired an improved catheter and method of use thereof for selectively delivering fluids to a body vessel, and draining fluids from the body vessel, in intermittent fashion. The improved catheter should be easy to use and selectively controllable.

SUMMARY OF THE INVENTION

The present invention achieves technical advantages as a catheter and method of use thereof having an internal balloon defined in a lumen allowing the selective occlusion of the lumen to control fluid flow therethrough. The lumen is further provided with proximal openings communicating with the ambient that can be selectively isolated from or rendered in communication with the lumen distal end by the selectively inflatable balloon therebetween.

In a first embodiment of the present invention, the catheter has a first lumen open at the catheter body distal end and a second lumen that is closed at the distal end, with a first opening defined between the first lumen and second lumen. Like the first embodiment, the catheter body has a second opening extending from the first lumen to the ambient, with the second opening being disposed proximal of the first opening. A first expandable balloon member is sealingly disposed across the first opening and is expandable to fully occlude the first lumen when pressure is applied to the second lumen. The first expandable balloon member thus selectively isolates or allows communications of the first lumen second opening and the first lumen distal opening. In this first embodiment, the catheter is preferably provided with a third lumen extending to the catheter body distal end and being isolated from the first lumen and the second lumen. In this embodiment, the third lumen has a sufficiently large diameter to allow oxygenated blood flow therethrough at a rate and pressure sufficient to perfuse the body. This catheter also preferably includes a second expandable double lobed balloon member disposed about the catheter body distal end with the catheter body second opening being disposed proximal the second balloon.

This first embodiment is ideal for delivering cardioplegia to arrest the heart and then perfusing the heart to restart the heart while facilitating an anastomosis when the catheter distal end is positioned upwardly into the ascending aorta. The second opening of the first lumen may be used to deliver cardioplegia, and also to selectively perfuse the aortic base of the heart by allowing communication of a portion of the oxygenated blood delivered from the third lumen into the ascending aorta back through the unoccluded first lumen and the first lumen second openings. Thus, the expandable first balloon in the first lumen can control the perfusion of the oxygenated blood to the aortic base. The double lobed balloon creates a bloodless site to facilitate the anastomosis while the heart is perfused.

According to the second embodiment of the present invention, the catheter comprises a catheter body extending from a proximal end to a distal end, the catheter body defining a first lumen and second lumen. The first lumen is characterized by being open at the catheter body distal end, whereby the second lumen is closed at the distal end. The catheter body has a first opening defined between the first lumen and the second lumen. The catheter body further comprises a second opening extending from the first lumen to the ambient, whereby the second opening is disposed proximal of the first opening. A first expandable balloon member is sealingly disposed across the first opening separating the first lumen and the second lumen. The first balloon member is selectively expandable to fully occlude the first lumen when pressure is applied to the second lumen such that the catheter body second opening is selectively isolated from the first lumen distal opening. By selectively inflating or deflating the first balloon member, the first lumen can be rendered open or occluded to control the fluid communication between the first lumen second opening and the distal opening of the first lumen. The catheter preferably comprises a second expandable balloon disposed about the catheter body distal end, wherein the catheter body second opening is disposed proximal this second balloon. The second balloon preferably has a pair of lobes defining a recess therebetween when inflated. According to this second embodiment, the catheter body preferably comprises a third lumen isolated from the first lumen and the second lumen, whereby the third lumen is in fluid communication with the second balloon. The catheter body may further include a fourth lumen extending to the catheter body distal end and which opens distal of the second balloon. The catheter may include an annular member defining an annular cavity about the catheter body distal end. This annular cavity has a plurality of annularly spaced openings and is in fluid communication with the fourth lumen.

This second embodiment is ideal for delivering cardioplegia to arrest the heart and then perfusing the heart to restart the heart while facilitating an anastomosis when the catheter distal end is positioned downwardly in the aorta toward the aortic base. Preferably, the first lumen has sufficiently large diameter to allow blood flow therethrough at a rate and pressure sufficient to perfuse a body via the second opening, whereby the first inner balloon is used to allow a portion of the blood flowing through the first lumen to communicate to the distal end to provide myocardial infusion. The double lobed outer balloon creates a bloodless site to facilitate an anastomosis while the heart is perfused. The fourth lumen can be used to deliver cardioplegia.

According to a first method of the present invention, the catheter body according to the first embodiment is used to perfuse a body by first positioning the catheter in the ascending aorta of the heart such that the catheter distal end is positioned upwardly into the aorta. Next, the body is perfused by delivering oxygenated blood via the large third lumen into the ascending aorta. Next, the first balloon is inflated via the second lumen to occlude the first lumen. Thereafter, the second double lobed balloon is inflated to occlude the aorta. Cardioplegia is then delivered to the aortic base to arrest the heart via the occluded first lumen and the first lumen proximal second opening. Thereafter, the first inner balloon is deflated such that a portion of the oxygenated blood perfusing the ascending aorta via the third lumen communicates back to the aortic base via the first lumen proximal second opening to perfuse the aortic base and restart the heart while the double lobed second balloon continues to occlude the aorta and creates a bloodless site for an anastomosis. In this embodiment, the third lumen has a sufficiently large diameter to allow oxygenated blood flow therethrough at a rate and pressure sufficient to perfuse the body. The first lumen may be used to vent the aortic base.

According to the second method of the present invention, the body is perfused using the catheter according to the second embodiment of the present invention. In this embodiment, the catheter is positioned downwardly in the aorta such that the catheter distal end extends downwardly towards the aortic base of the heart. Next, the body is perfused by delivering oxygenated blood into the ascending aorta via the first lumen and the first lumen second opening. Thereafter, the first inner balloon is inflated by applying pressure to the second lumen to occlude the first lumen where the body is continued to be perfused by delivering blood into the ascending aorta via the first lumen second opening. Thereafter, the second double lobed balloon is inflated to occlude the aorta. Cardioplegia is then delivered via the fourth lumen to arrest the heart. Thereafter, the first balloon is deflated to perfuse the coronaries at the aortic base with oxygenated blood via the first lumen distal end to restart the heart while the two lobe second balloon continues to occlude the aorta and creates a bloodless region to facilitate an anastomosis.

In both methods of the present invention the second balloon preferably has a pair of lobes defining a bloodless region therebetween in the aorta when inflated to facilitate an anastomosis at the bloodless region while perfusing the aortic base.

According to a third embodiment of the invention, there is in combination a first catheter having a first lumen extending therethrough, and a second catheter having an inflatable balloon positioned within the first catheter first lumen, wherein the balloon is selectively inflatable to selectively occlude the first lumen. This general purpose combination can be used in a third method of the present invention to selectively deliver fluids to or drain fluids from a body vessel by positioning the first catheter in the body vessel, communicating a fluid between the first catheter first lumen and the body vessel, and then selectively expanding the second catheter balloon within the first catheter first lumen to selectively control the flow rate of the fluid through the first lumen to the body vessel, or to selectively control the flow rate of the fluid from the first body vessel through the first lumen.

DESCRIPTION OF THE PREFERRED EMBODIMENT

Figure 1:
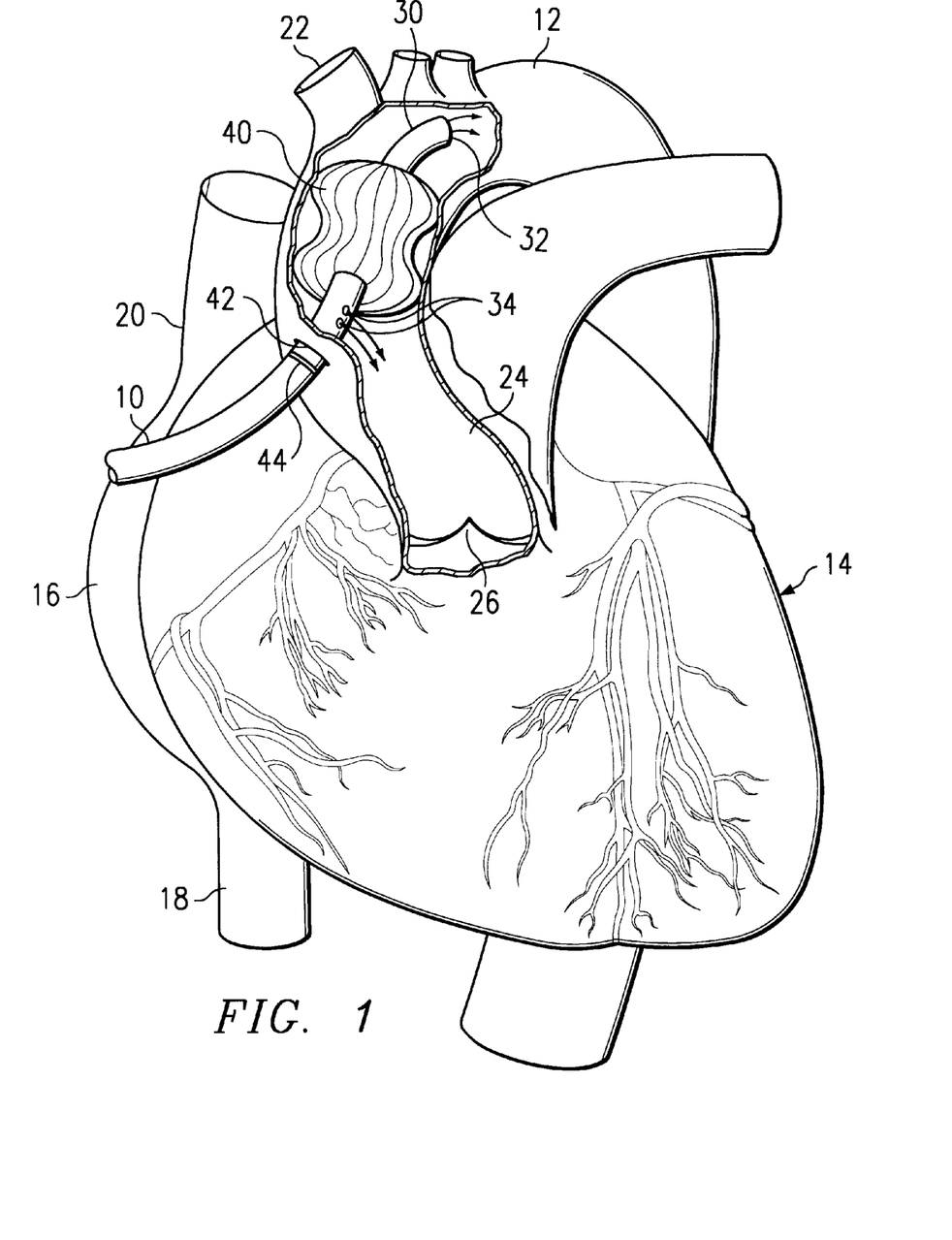
FIG. 1 is an illustration of a catheter according to a first embodiment of the present invention and a method of use thereof with the catheter extending upwardly into the ascending aorta delivering oxygenated blood out the distal end thereof, and selectively providing cardioplegia and myocardial infusion in antegrade flow through the proximal openings to the aortic base by selectively controlling the inflation of the inner occluding balloon in the first lumen while creating a bloodless site for an anastomosis.

Referring now to FIG. 1, there is shown generally at 10 a fluid delivery and fluid drainage catheter according to a first embodiment of the invention. Catheter 10 is seen to be used in a first method of the present invention to perfuse the body with oxygenated blood via the ascending aorta while selectively delivering cardioplegia and providing myocardial infusion to the aortic base in antegrade flow. Catheter 10 is seen to be disposed through an incision created in the aorta wall with the catheter distal end extending upwardly into the ascending aorta 12 of heart 14. For reference, the right atrium is shown at 16, with the inferior vena cava being shown at 18 and the superior vena cava being shown at 20. The Brachiocephalie Artery is shown at 22, with the aortic base being shown at 24 and the aortic valve being shown at 26.

Catheter 10 is seen to infuse oxygenated blood into the ascending aorta from distal end 30 via a distal opening 32. A double lobed balloon 40 is shown in the inflated position within the ascending aorta to occlude and separate the perfused ascending aorta from the aortic base 24 as shown. Proximal openings 34 are used to intermittently deliver cardioplegia to the aortic base 24 to arrest the heart as desired, whereby balloon 40 isolates the cardioplegia from the ascending aorta. Openings 34 are also used to selectively and intermittently deliver a portion of the infused oxygenated blood from the ascending aorta to the aortic base to perfuse the heart coronaries in antegrade flow. This myocardial infusion provides oxygenated blood to the coronaries to insure the myocardium meets its oxygen demand. Openings 34 may also be used to vent the aortic base as needed. An interior occluding balloon of a lumen in communication with proximal openings 34, as will be described shortly, facilitates the selected intermittent delivery of cardioplegia and oxygenated blood via openings 34. Catheter 10 is seen to be inserted through an incision 42 created by the physician in the ascending aorta wall. The catheter 10 is provided with a marker or indicia 44 to help the physician position the catheter within the ascending aorta.

Figure 2:
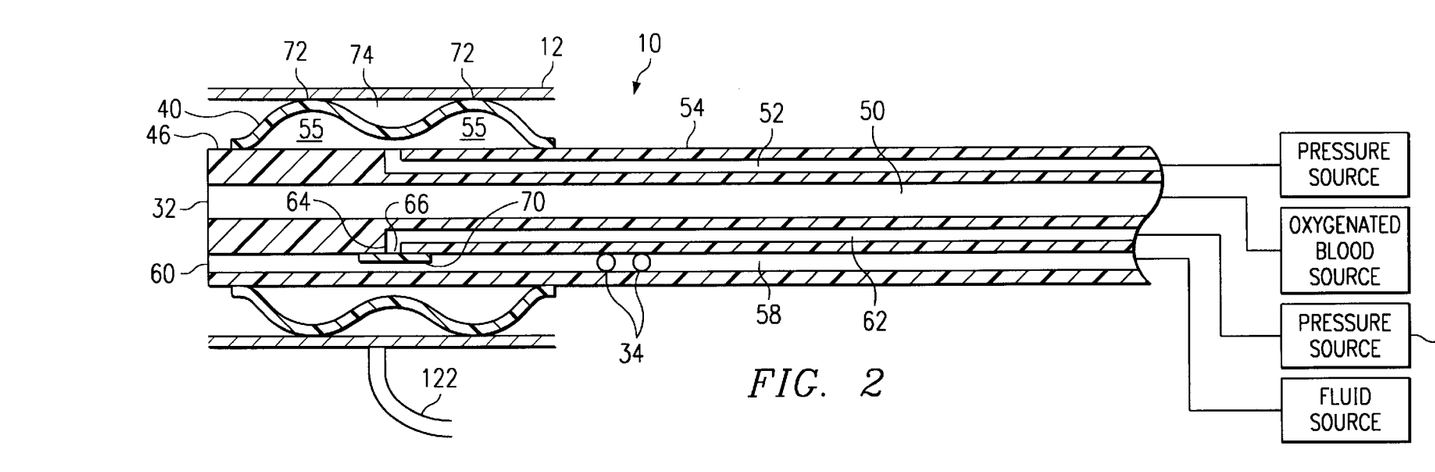
FIG. 2 is a cross sectional view of the catheter of FIG. 1 illustrating an interior occlusion balloon in the uninflated position of a first fluid delivery lumen.

Referring now to FIG. 2, there is illustrated a cross sectional view of catheter 10. FIG. 2 will be described in reference to FIG. 1 to illustrate and fully teach the advantageous features of the catheter and a preferred method of use thereof, with the method shown in FIG. 1 being just one of several uses of the catheter 10. Other uses of catheter 10 are intended and suitable for delivering fluids to or draining fluids from a body vessel.

Referring to FIG. 2, catheter 10 is seen to include a large main lumen 50 extending concentrically along the length thereof to distal opening 32. Catheter 10 is also seen to include a balloon inflation lumen 52 extending through the catheter body 54. A smaller fluid delivery or fluid drainage lumen 58 extends along the length thereof and terminates at a distal opening 60 proximate the distal opening 32 of larger lumen 50. Lumen 58 has proximal openings 34. A fourth lumen 62 is seen to extend through catheter body 54 and terminates at a closed end 64, whereby the closed end 64 has an opening 66 extending between the lumen 62 and the lumen 58. Sealingly disposed across this opening 66 is an elastic expandable balloon member 70 fluidly isolating the closed end 64 of lumen 62 from the fluid delivery/drainage lumen 58, as shown. In FIG. 2, this expandable balloon 70 is shown in the unexpanded position such that delivery/drainage lumen 58 is open with distal opening 60 in fluid communication with proximal openings 34. Balloon 40 is seen to have a pair of lobes 72 forming a recess therebetween and defining a cavity 74 therebetween in combination with the vessel wall 12. Cavity 74 provides a bloodless region between the lobes 72 proximate the vessel wall to facilitate anastomosis to the vessel 12 proximate cavity 74. Balloon inflation lumen 52 is seen to include an opening 53 opening into a cavity 55 defined by balloon 40.

Figure 3:
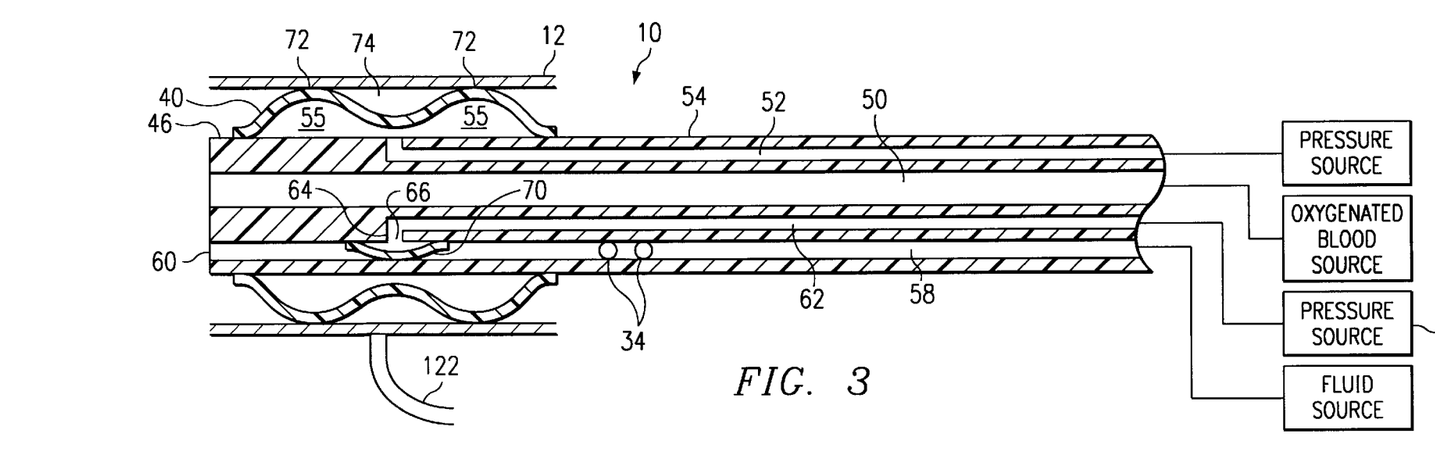
FIG. 3 is a cross sectional view of the catheter of FIG. 1 illustrating the inner occlusion balloon in the inflated position isolating the distal end of the first fluid delivery lumen from the proximal openings opposite the interior occlusion balloon.

Referring to FIG. 3, when a fluid pressure is provided to lumen 62 by pressure source 64, the expandable balloon 70 is seen to expand into the fluid delivery/drainage lumen 58 and occlude the lumen such that the distal opening 60 is fluidly isolated from the proximal openings 34. By selectively providing pressure to or removing the fluid pressure from the lumen 62, the expansion of inner balloon 70 can be selectively and controllably established to selectively and controllably occlude the fluid delivery lumen 58, thereby selectively isolating or communicating the proximal openings 34 from the distal opening 60.

To illustrate a first method of the present invention, referring to FIG. 1 it can be seen that the catheter distal end is inserted through incision 42 in aorta 12 and positioned upwardly into the ascending aorta 12 with the distal end 30 of the catheter positioned into the ascending aorta. The ascending aorta is infused with oxygenated blood to infuse the body via the large lumen 50. Lumen 50 has a diameter sufficiently large to deliver the oxygenated blood at a suitable flow and a suitable pressure to perfuse the body. Thereafter, the double lobed balloon 40 is inflated via lumen 52 to occlude the aorta as shown in FIG. 2. Next, the inner occluding balloon 70 is inflated by applying a fluid pressure to lumen 62 via source 64 thereby occluding the fluid delivery lumen 58 at balloon 70, as shown in FIG. 3. Then, cardioplegia may be delivered via lumen 58 and proximal openings 34 into the aortic base 24 to arrest the heart as desired. The double lobed balloon 40 isolates the cardioplegia from the ascending aorta. Lumen 58 and openings 34 may also be used to vent the aortic base 24 to remove air, excess cardioplegia, and/or blood as desired. Thus, fluid lumen 58 can be used to both infuse and vent fluids from a body vessel when inner balloon 70 is in the expanded occluding position.

Next, the fluid pressure to lumen 62 is removed such that the inner balloon 70 retracts and establishes fluid communication between distal opening 60 and proximal opening 34. By continuing to infuse the ascending aorta with oxygenated blood via large lumen 50, a portion of this oxygenated blood will communicate back through distal opening 60 into lumen 58 and exit via proximal openings 34 to provide myocardial infusion to the aortic base 24 in antegrade flow. The pressure in the aortic arch at the distal end of catheter 10 is higher than the aortic base pressure and causes a portion of the oxygenated blood to flow from opening 32 to opening 60 and back eventually to proximal openings 34.

It is noted that the openings 34 are proximal the second occluding balloon 40 and the inner balloon 70 disposed across the opening 66. The orientation of the inner balloon 70 between the distal opening 60 and the proximal openings 34 is one advantageous feature providing versatility whereby the lumen 58 can both infuse fluids as well as drain fluids from a body cavity. The method of FIG. 1 illustrates how openings 34 can be used to both deliver cardioplegia and oxygenated blood as well as vent the aortic base. The inner balloon 70 essentially operates as a pneumatic valve to allow the selective communication of the large lumen 50 distal end 32 to the smaller lumen 58 to provide myocardial infusion into the aortic base in an intermittent and controlled fashion.

Figure 4:
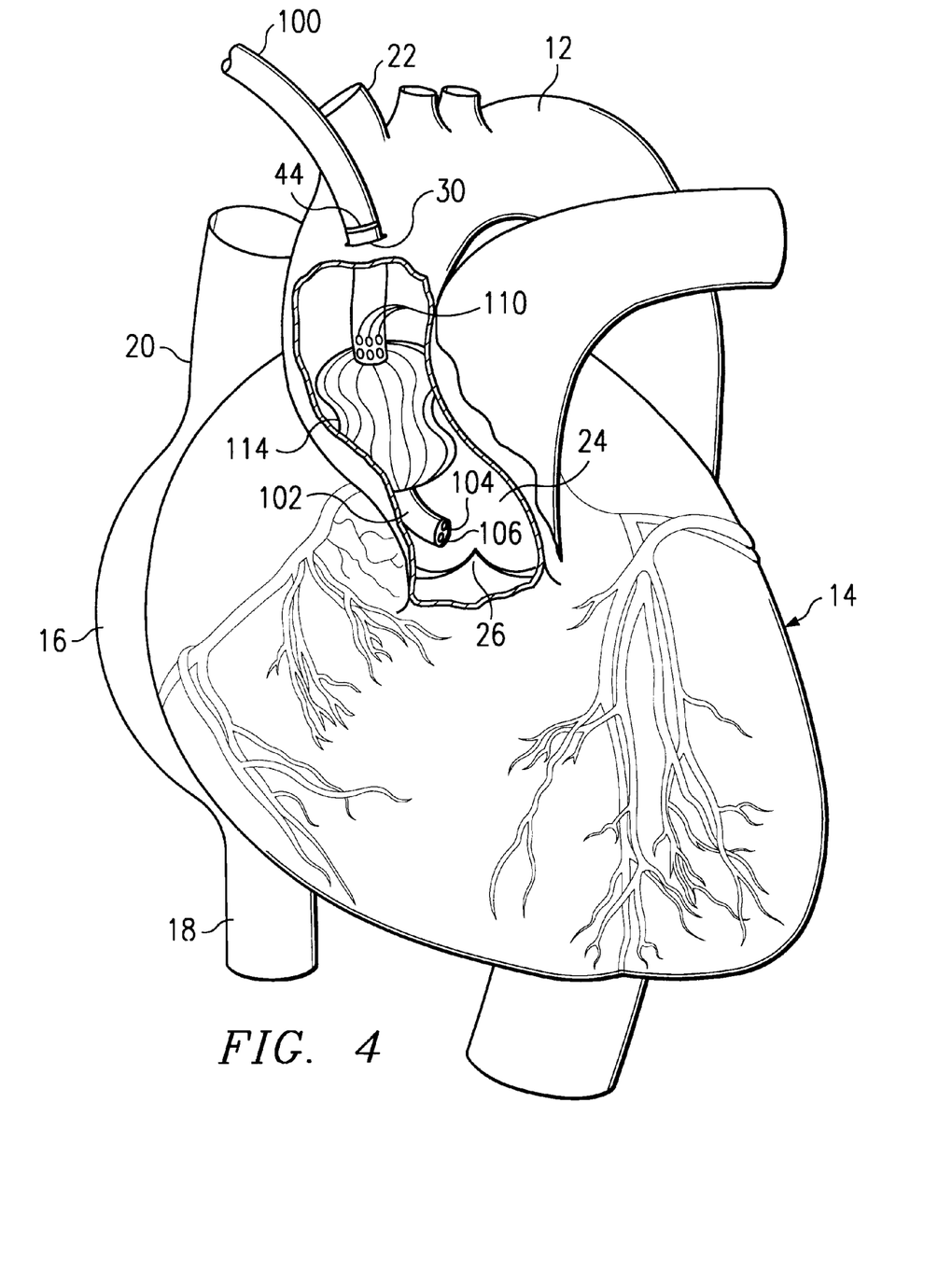
FIG. 4 is an illustration of a catheter according to a second embodiment of the present invention and method of use thereof illustrating the catheter being inserted downwardly into the ascending aorta with the catheter distal end positioned in the aortic base proximate the aortic valve, whereby oxygenated blood is selectively infused into the aortic base to provide myocardial infusion in antegrade flow by controlling the inflation of an interior balloon while creating a bloodless site for an anastomosis.

Referring now to FIG. 4, there is illustrated a catheter of a second embodiment of the present invention shown as catheter 100, and a method of use thereof. Catheter 100 is seen to be inserted through the incision 30 of aorta 12 downwardly, with the distal end 102 being positioned into the aortic base 24 and proximate the aortic valve 26. Catheter 100 has a catheter body 103. The distal end of catheter 100 has a distal opening 104 and circumferential openings 106 which will be described shortly. Catheter 103 is also seen to include a plurality of proximal openings 110 disposed on the proximal side of a double lobed balloon 114.

Figure 5:
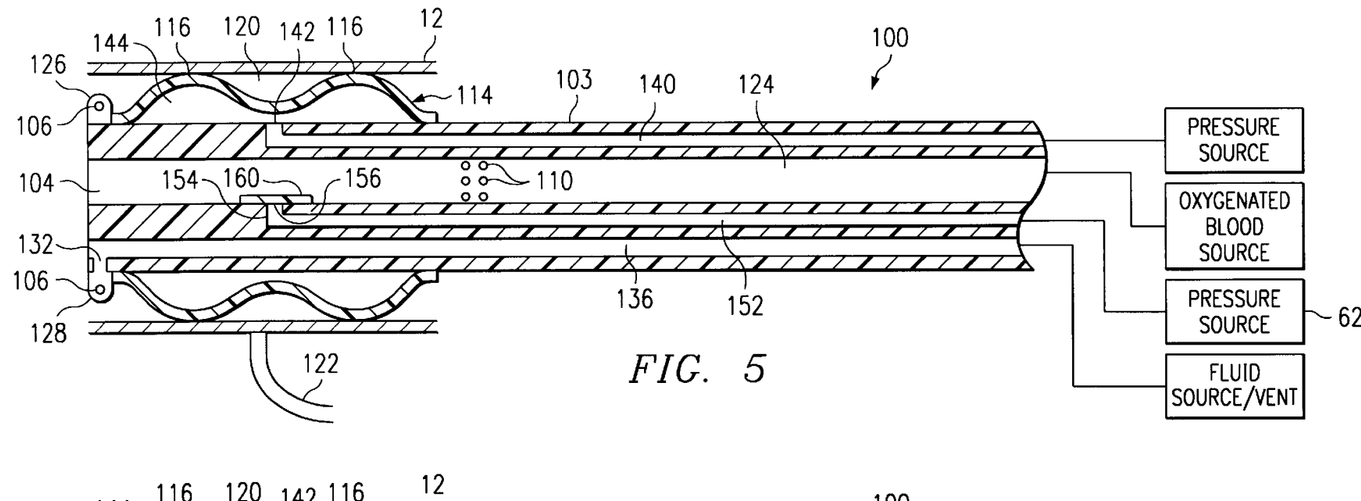
FIG. 5 is a cross sectional view of the catheter of FIG. 4 illustrating the interior occlusion balloon in the uninflated position and residing within the larger first lumen.

Referring now to FIG. 5, there is shown a cross sectional view of catheter 100 illustrating double lobed balloon 114 in the expanded position. The pair of balloon lobes 116 define a cavity 120 therebetween in combination with the vessel wall 12 when inflated. The double lobed balloon 116 provides a bloodless region in cavity 120 to facilitate an anastomosis 122 at this site while the aorta is occluded and the aortic base is perfused to provide myocardial infusion.

Catheter body 103 is seen to include a first large lumen 124 concentrically extending from a proximal end of the catheter body to the distal opening 104. Disposed about the distal end of catheter body 103 is seen to be an annular member 126 defining an annular cavity 128. Annular member 126 is seen to include the plurality of annularly spaced openings 106 communicating the annular cavity 128 with the ambient. Catheter body 103 is seen to have an opening 132 communicating the annular cavity 128 with a lumen 136 extending from a closed distal end to the proximal end of the catheter. Lumen 136 and openings 106 facilitate the delivery of cardioplegia to the aortic base 24 as necessary. Lumen 136 and openings 106 also facilitate the venting of the aortic base, such as the removal of excess cardioplegia or blood as desired.

Catheter 100 also includes a balloon inflation lumen 140 in fluid communication via an opening 142 with a balloon cavity 144 defined by balloon 116. Catheter body 103 is further seen to include the plurality of proximal openings 110 defined therethrough communicating lumen 124 with the ambient. The catheter body 103 is also seen to have a lumen 152 terminating at a closed end 154. Closed end 154 has an opening 156 communicating with lumen 124, and is sealingly separated therefrom by an inflatable inner balloon 160. As shown in FIG. 5, inflatable balloon 160 is in the unexpanded position thereby allowing the distal opening 104 to communicate with the plurality of proximal openings 110 of passageway 124.

Figure 6:
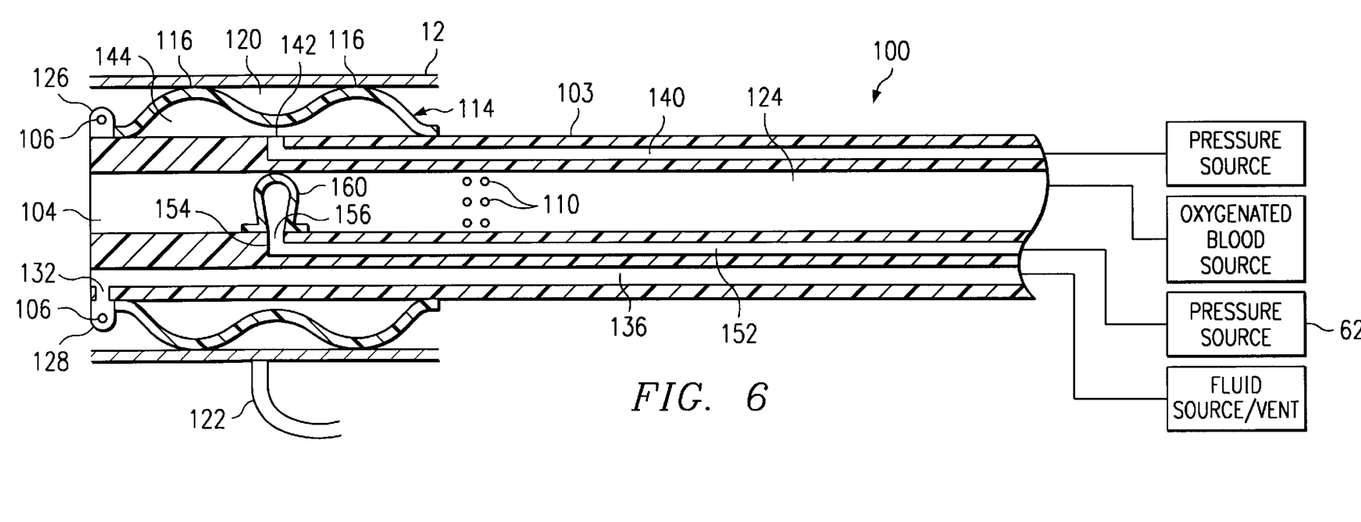
FIG. 6 is a cross sectional view of the catheter of FIG. 4 illustrating the interior occlusion balloon in the inflated position occluding the larger lumen used for selectively perfusing the aorta, the inner balloon selectively isolating the proximal perfusion openings from the lumen distal end.

Referring to FIG. 6, the inflatable balloon 160 is shown to be in the inflated position to occlude the lumen 124 and isolate the distal opening 104 from the plurality of proximal openings 110. The internal inflatable balloon 160 is inflated by applying a fluid pressure via lumen 152 to selectively occlude the lumen 124, as shown in FIG. 6, such as when delivering cardioplegia to the aortic base via lumen 136. It is noted and advantageous that the plurality of openings 110 are proximal of the inner inflatable balloon member 160 and the outer double lobed balloon 114 which selectively isolate or communicate the proximal openings 110 with the distal openings 104.

According to a second preferred method of the present invention, catheter 110 is suited for use to selectively perfuse the ascending aorta via the plurality of openings 110, and also to selectively provide myocardial infusion to the aortic base 24 proximate aortic valve 26 by selectively inflating or deflating the inner balloon 160 to selectively occlude or open the large inner lumen 124.

The following method illustrates one preferred method of the present invention and a suitable use for catheter 100, although other suitable uses for catheter 100 are envisioned for selectively infusing or venting fluid from a body cavity or body vessel.

Referring to FIG. 4, catheter 100 is seen to be inserted through the incision 30 of aorta 12 and advanced downwardly such that the distal end of the catheter is positioned in the aortic base 24 proximate the aortic valve 26. Next, the ascending aorta 12 is perfused by delivering oxygenated blood via the large lumen 124 such that oxygenated blood is dispensed via the plurality of proximal openings 110 and distal opening 104 into the ascending aorta to perfuse the body. Thereafter, the double lobed outer balloon 114 is inflated by applying a fluid pressure to the balloon inflation lumen 140. The inflated double lobed balloon 114 expands to engage the inner wall of aorta 12 as shown to provide the bloodless region or cavity 120, as shown in FIG. 5 and FIG. 6, to facilitate an anastomosis. Next, the inner balloon 160 is inflated as shown in FIG. 6 by applying a fluid pressure to lumen 152. The inner inflated balloon 160 occludes the large lumen 124 to isolate the distal opening 104 from the proximal openings 110. Oxygenated blood will continue to perfuse from proximal openings 110 into the ascending aorta 12.

Next, cardioplegia can be delivered via lumen 136 and dispensed via openings 130 into the aortic base 24 and aortic valve 26 to arrest the heart and allow attaching the distal end of an anastomosis to the heart coronaries. The aortic base may also be vented via lumen 136 and openings 130 as desired. The double lobed balloon 116 and the inner balloon 160 isolate the cardioplegia dispenses into the aortic base from the ascending aorta.

Next, using the inner balloon 160, myocardial infusion of the aortic base 24 can be provided in antegrade flow by selectively lowering the fluid pressure in lumen 152 to allow the inner balloon 160 to collapse, thereby communicating the distal opening 104 with the large main lumen 124. Thus, a portion of the oxygenated blood flowing through lumen 124 will advance to the distal opening 104 and infuse the coronaries at the aortic base 24 to assist in restarting the heart. The inner balloon 160 selectively occludes the inner lumen 124 to allow the selective myocardial infusion of oxygenated blood into the aortic base 24 via opening 104 while simultaneously perfusing the ascending aorta. The large double lobed balloon 114 remains in the expanded position to occlude the aorta and keep the aortic base 24 separate from the ascending aorta about the catheter, as shown. The single lumen 124 provides arterial return of oxygenated blood into the ascending aorta while providing myocardial infusion to ensure the myocardium meets its oxygen demand. The expanded double lobed lumen 114 advantageously provides the bloodless region 120 to facilitate a clear site for attaching the proximal end of an anastomosis 122 to be performed by the surgeon as the heart is restarted, prior to the completion of the anastomosis. Cardioplegia can be subsequently delivered via lumen 136 and openings 130 if needed by first reinflating the inner balloon 160 to isolate the opening 104 from the proximal openings 110 during the delivery of cardioplegia.

Figure 7:
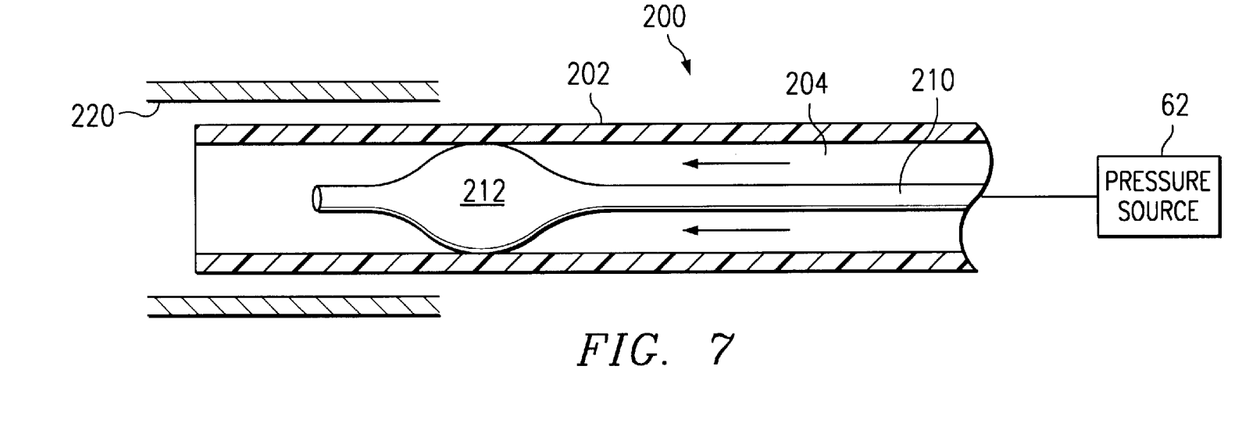
FIG. 7 is an illustration of a third embodiment of the present invention including a catheter balloon inserted into and selectively occluding a second catheter second lumen to control the flow of fluid through the second lumen.
Figure 8:
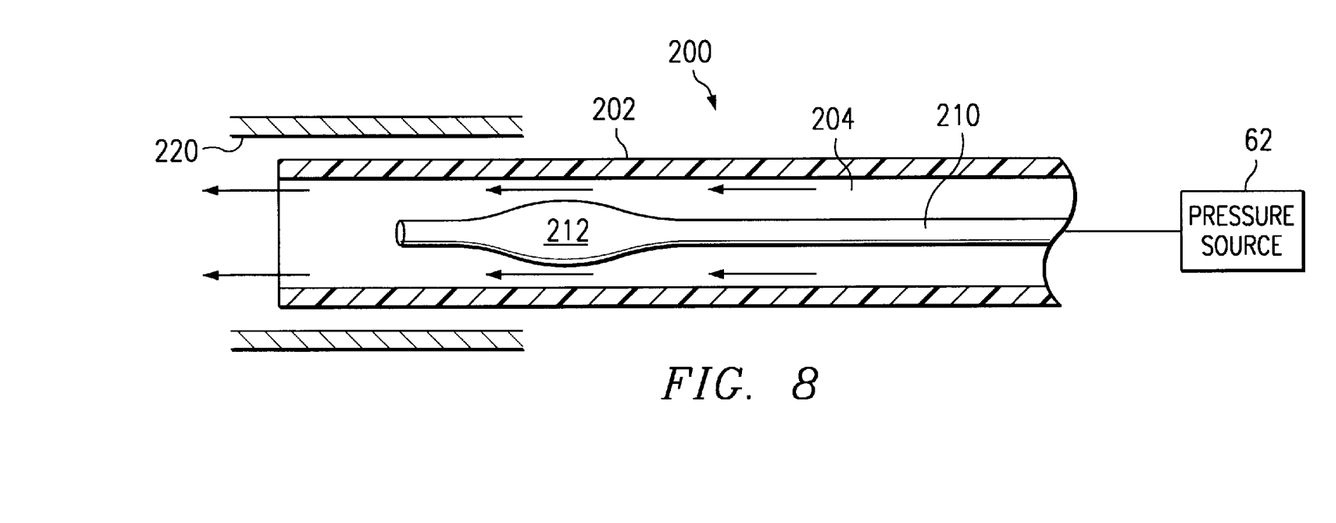
FIG. 8 is an illustration of the catheter combination of FIG. 7 illustrating the inner balloon in a deflated position to allow fluid communication through the second lumen.

Turning now to FIG. 7, there is shown a third embodiment of the present invention illustrated as a catheter combination 200. Catheter combination 200 includes a first catheter 202 having an inner lumen 204 extending the length thereof. A second catheter 210 having a distal inflatable balloon member 212 is seen to be advanced within the inner lumen 204 of first catheter 202. Fluid can be delivered to a body vessel 220, or a fluid can be vented therefrom, via the first lumen 204 of first catheter 202 by selectively deflating balloon 212 as shown in FIG. 8. With balloon 212 in the deflated position, fluid can readily flow through first lumen 204 to allow the venting or delivery of fluid from body vessel 220 via first lumen 204.

However, to inhibit or prevent the delivery or venting of fluid from the body vessel 220, the inner balloon 212 is inflated as shown in FIG. 7. This inflated inner balloon 212 occludes the inner lumen 204 of first catheter 202 to prevent flow therethrough. Thus, the inner second catheter 210 including balloon 212 is essentially a pneumatic valve allowing or inhibiting the communication of a fluid through first lumen 204 of the first catheter 202.

The catheter combination and method shown in FIG. 7 and FIG. 8 is suited for a wide variety of uses in medical procedures including delivering and draining fluids from a body vessel, including the ascending aorta of the heart. The catheter combination is suited for use in the embodiments of FIG. 1 and FIG. 4 if desired.

In summary, the present invention comprises several embodiments of catheters and methods of use thereof for delivering fluids to and draining fluids from a body vessel in intermittent fashion by using an inner balloon to selectively occlude a delivery/draining lumen. The inflation and deflation of the inner balloon is used to selectively isolate or communicate an opening at the distal end of the catheter from a proximal opening. The catheter may be provided with a second outer balloon for selectively occluding the body vessel. The inner balloon controls the communication of proximal openings to the distal end of the catheter, such as to intermittently provide myocardial infusion in antegrade flow as shown in FIG. 1 and FIG. 4. The various catheters of the present invention can be advanced upwardly or downwardly into the ascending aorta. Cardioplegia can be intermittently delivered with intermittent myocardial infusion using a common or different lumen. A bloodless region can be provided between the lobes of the inflated doubled lobed outer balloon to facilitate attaching the proximal end of an anastomosis as the heart is restarted and the myocardium is infused. The catheters of the present invention find particular use whereby the proximal openings are selectively isolated from the distal opening of a lumen by the inflatable inner balloon disposed therebetween. As illustrated in the various Figures, the inner balloon advantageously allows the delivery of fluids to, or the venting of fluids from, the body vessel, in intermittent fashion such as the aorta of the heart. The catheters of the present invention are shown in appended uses in the various Figures to illustrate preferred methods of use. However, other methods of use of the catheters are anticipated and limitation to providing aortic perfusion and myocardial infusion is not to be inferred. The catheters of the present invention provide significant technical advantages by allowing a physician to perfuse an aorta and selectively provide myocardial infusion in antegrade flow using a single lumen of a aortic perfusion catheter. The use of fluid pressure to control the selective inflation or deflation of the inner balloon to occlude the lumen provides a simple control device comprising a pneumatic valve to control the drainage or delivery of fluids in intermittent fashion.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

I claim:

1. A catheter for perfusing a human body via in an aorta, comprising:

a catheter body extending from a proximal end to a distal end, said catheter body having an exterior surface and defining a first lumen and a second lumen, wherein said first lumen is open at said catheter body distal end and said second lumen is closed, wherein said first lumen has a sufficiently large diameter to allow blood flow therethrough at a rate and pressure sufficient to perfuse a human body via an aorta, said catheter body having an first opening defined between said first lumen and said second lumen, said catheter body further having a proximal second opening extending from said first lumen to the exterior surface, said second opening being disposed proximal said first opening; and a first expandable balloon member sealingly disposed across said first opening, said first balloon member being expandable to fully occlude said first lumen when pressure is applied to said second lumen such that said catheter body proximal second opening is isolated from said first lumen distal opening.

2. The catheter as specified in claim 1 wherein said catheter further comprises a second expandable balloon member disposed about said catheter body distal end, wherein said catheter body proximal second opening is disposed proximal said second balloon.

3. The catheter as specified in claim 2 wherein said second balloon has a pair of lobes defining a recess therebetween when inflated.

4. The catheter as specified in claim 3 wherein said catheter body further comprises a third lumen isolated from said first lumen and said second lumen, said third lumen being in fluid communication with said second balloon.

5. The catheter as specified in claim 4 wherein said catheter body further includes a fourth lumen extending from said catheter body proximal end to said catheter body distal end and opening distal of said second balloon.

6. The catheter as specified in claim 5 wherein said catheter further includes an annular member defining an annular cavity about said catheter body distal end, said annular cavity having a plurality of annularly spaced openings and being in fluid communication with said fourth lumen.

7. The catheter as specified in claim 1 wherein said catheter further comprises a third lumen extending to said catheter body distal end being isolated from said first lumen and said second lumen, wherein said third lumen has a sufficiently large diameter to allow blood flow therethrough at a rate and pressure sufficient to perfuse a human body via an aorta.

* * * * *